United States Patent [19]
Forester

[11] Patent Number: 4,762,719
[45] Date of Patent: Aug. 9, 1988

[54] POWDER FILLED COUGH PRODUCT

[76] Inventor: Mark Forester, 8 Oak Park Dr., Convent Station, N.J. 07961

[21] Appl. No.: 894,068

[22] Filed: Aug. 7, 1986

[51] Int. Cl.⁴ .......................... A61K 9/20; A61K 9/28; A61K 9/48

[52] U.S. Cl. ..................... 424/440; 424/451; 424/479; 514/777; 514/849; 514/850; 514/853; 514/948

[58] Field of Search ............... 424/14, 16, 21, 35, 424/37, 440; 514/948

[56] References Cited

U.S. PATENT DOCUMENTS

| | | | |
|---|---|---|---|
| 352,466 | 11/1886 | Huttemeyer | 424/35 |
| 1,046,056 | 12/1912 | Drake | 424/35 |
| 2,253,800 | 8/1941 | Myers et al. | 424/35 |
| 2,311,923 | 2/1943 | Lautmann | 424/35 |
| 2,580,683 | 1/1952 | Kreuger | 424/37 |
| 3,515,781 | 6/1970 | Steinberg | 424/37 |
| 3,536,074 | 10/1970 | Aufhauser | 424/37 |
| 3,644,613 | 2/1972 | Moeller et al. | 426/3 |
| 4,196,189 | 4/1980 | Raaf et al. | 424/37 |
| 4,292,304 | 9/1981 | Barels et al. | 424/37 |
| 4,372,942 | 2/1983 | Cimiluca | 424/14 |

FOREIGN PATENT DOCUMENTS

| | | | |
|---|---|---|---|
| 799450 | 11/1968 | Canada | 424/37 |
| 829269 | 12/1969 | Canada | 424/37 |

Primary Examiner—Shep K. Rose
Attorney, Agent, or Firm—Ronald G. Goebel; Bruce M. Collins

[57] ABSTRACT

A cough drop is provided comprising a hard candy outer shell and a powdered centerfill containing a rapidly-dissolving powder such as dextrose monohydrate and an active ingredient such as menthol and eucalyptus which is preferably in the form of a liquid blend and a spray-dried powder. The hard candy outer shell also contains menthol and eucalyptus as a liquid blend.

When the outer shell is dissolved in the mouth or the centerfill is bitten into, the rapidly-dissolving powder acts to enhance the active-ingredient's activity in the mouth so that a discernible vaporization of active-ingredient is felt.

20 Claims, No Drawings

POWDER FILLED COUGH PRODUCT

BACKGROUND OF THE INVENTION

This invention is concerned with a cough drop having a center powder filling which permits the active-ingredients in the cough drop to be rapidly released, thus yielding a perceptible vaporization in the mouth.

Cough drops are generally comprised of a hard candy matrix comprised of sucrose and corn syrup and active ingredients such as menthol and eucalyptus which are sealed in the hard candy matrix. As the hard candy matrix ages in the mouth the sucrose portion begins to crystallize or "grain" allowing some of the active ingredient to escape from the hard candy matrix.

The present invention, on the other hand, provides a cough drop product which is center-filled with a fast-dissolving powder and active ingredient. When the cough drop outer shell is dissolved in the mouth or bitten to its center to expose the center-filling the fast-dissolving powder during dissolution in the mouth releases the active ingredient producing a markedly perceivable feeling of vaporization of active ingredient into the oral and nasal cavities.

SUMMARY OF THE INVENTION

The present invention comprises a comestible, particularly a cough drop, which includes a hard candy outer shell which encloses a centerfill containing a rapidly-dissolving powder such as dextrose monohydrate and an active-ingredient such as menthol-eucalyptus.

The hard candy outer shell is comprised of a hard candy base such as sucrose and corn syrup and an active-ingredient such as menthol-eucalyptus in the form of a liquid blend. The menthol-eucalyptus in the centerfill is preferably in the form of a liquid blend and spray-dried powder.

The cough drop is prepared by first cooking the candy base and adding to the partially coated candy mass the liquid blend of menthol and eucalyptus. An outer shell of this combination is placed around a powder center filling tube and filled with a powder blend comprising a mixture of the rapidly dissolving powder and active ingredients. The resulting cough drop can then be tabletted using conventional candy forming equipment.

DETAILED DESCRIPTION OF THE PREFERRED EMBODIMENTS

The rapidly-dissolving powders used in the invention include dextrose monohydrate, xylitol, sorbitol or sucrose with dextrose monohydrate being preferred. Such powders, when released into the mouth, enhance active ingredient release to provide the aromatic vaporization of the ingredient into the oral and nasal cavities. It is desirable, but not mandatory, that the center-filled powder have a negative heat of solution to accentuate the cooling effect of the active ingredients. For this reason, dextrose monohydrate, xylitol and sorbitol are particularly desirable. Generally the amount of rapidly-dissolving powder should comprise from 0.1% to 75% by weight of the total centerfill and perferably from 5% to 35% by weight. By rapidly-dissolving it is meant that the powder will solubilize in the aqueous based-saliva and fluids in the amount to the extent of at least 1% in less than one minute.

The preferred active ingredient is a combination of menthol and eucalyptus which is also incorporated into the center of the cough drop with the rapidly-dissolving powder. The menthol-eucalyptus may also be in the form of a powder but preferably it is combined with the rapidly-dissolving powder as both a liquid blend and a spray-dried powder. The liquid blend should comprise equal parts by weight of menthol and eucalyptus and the total liquid blend should comprise from 0.002% to 2.00% by weight of the total centerfill and preferably from 0.002% to 0.004% by weight. The preferred spray dried menthol-eucalyptus powder can comprise from 90% to 10% by weight menthol to from 90% to 10% by weight eucalyptus and preferably from about 50% by weight menthol to 50% by weight eucalyptus. The spray-dried menthol-eucalyptus may be obtained by spray drying a blend of menthol and eucalyptus on a carrier or by combining spray dried menthol on a carrier and eucalyptus on a carrier. Suitable carriers include starch dextrin, gum arabic or the like and combinations thereof. Generally the amount of spray-dried menthol eucalyptus should comprise from 0.1% to 35% by weight and preferably from about 0.2% to 25% by weight of the total centerfill.

The hard candy shell comprises a candy base and active ingredient but may also include additional ingredients such as food grade acids, natural and artificial flavors and artificial sweeteners.

The preferred candy base comprises sucrose and corn syrup although other candy bases may be used including hydrogenated starch hydrolysate, combinations of hydrogenated starch hydrolysate and polydextrose powder or high fructose corn syrup or sucrose and polydextrose, for example. When sucrose and corn syrup are employed, the sucrose should comprise from 10% to 80% by weight of the total hard candy shell and preferably from 50% to 65% by weight. The corn syrup should comprise from 20% to 90% by weight of the shell and preferably from 25% to 35% by weight. The active ingredient in the shell is also preferably menthol and eucalyptus which is added to the candy base as oils. The menthol and eucalyptus are employed in equal proportions and as a combination should comprise from 0.003% to 2% of the total shell and preferably from 0.010 to 0.2% by weight of the shell. The active ingredient should comprise from 0.001 to 30% by weight of the total shell and preferably from 0.005% to 10% by weight.

The flavors which may be employed in the hard candy shell include both natural and synthetic flavors, namely: citrus oils, such as cherry, lemon, orange, lime, etc.; essential oils, such as peppermint, spearmint, and methyl salicylate (oil of wintergreen); and synthetic flavors. Generally these flavors should comprise from 0.1% to 10% by weight of the total shell and preferably from 0.1% to 2% by weight.

Food grade acids useful in the invention include, but are not limited to, citric acid, lactic acid, isocitric acid, malic acid, fumeric acid, succinic acid, adipic acid, and tartaric acid. The amount of acid should comprise from 0.1% to 5% by weight of the shell and preferably from 0.1% to 2% by weight.

The shell may optionally include artificial sweeteners, such as sodium, calcium or ammonium saccharin salts, dihydrochalcones, glycyrrhizin, dipotassium glycyrrhizin, glycyrrhizic acid ammonium salts, L-aspartyl-L-phenylalanine methyl ester, as well as *Stevia rebaudiana* (Stevioside) *Richardella dulcifica* (Miracle Berry), *Dioscoreophyllum cumminsii* (Serendipity Berry), cyclamate salts, sucralose, acesulfam-K, thaumatin, hernandulcin, and various dipeptide derivatives and the like, or mixtures thereof. The amount of artificial sweetener may comprise from 0.001% to 5.0% by weight of the total shell. The hard candy shell should comprise from 55% to 99.9% by weight of the total weight of the cough drop and preferably from 85% to 95% by weight.

To prepare the cough drop product, the sucrose nd corn syrup are cooked to between 260° and 280° F. under vacuum. The menthol and eucalyptus oil are then thoroughly mixed into this candy in the molten state. Optional ingredients such as food grade acids, flavorants and artificial sweeteners, if desired are then added to the candy mass. An outer shell is then formed around a powder center filling tube in a heated candy batch-former. Next the powder centerfill consisting of a mixture of rapidly-dissolving powder, menthol-eucalyptus liquid blend and menthol-eucalyptus spray dried powder is added to the powder centerfilling tube to fill the center. The cough drop product having candy shell and centerfill is then tabletted with conventional candy forming equipment.

When placed in the mouth and the centerfill is exposed due to dissolution of the outer shell or by biting into the center, the powdered centerfill containing the rapidly-dissolving powder enhances the release of active ingredient into the oral and nasal cavities. The result is rapid delivery of the active ingredient coupled with a sensation of vaporization of the active ingredient into those cavities.

In order to more completely describe the present invention, the following Examples are given.

EXAMPLE 1

In this Example, a powder-filled cough drop can be prepared according to the invention having the composition as shown below in Table 1.

TABLE 1

| INGREDIENT | PARTS BY WEIGHT |
|---|---|
| Part A | |
| Hard Candy (0.5-3% moisture) (60/40% ratio sucrose and corn syrup by solids basis) | 99.970 |
| Menthol-eucalyptus liquid blend | −0.030 |
| | 100.00% |
| Part B | |
| Dextrose monohydrate | 99.85 |
| Menthol-eucalyptus liquid blend | 0.030 |
| Menthol-eucalyptus spray dried powder (Based on 0.1-40% actives, menthol-eucalyptus) | 0.120 |
| | 100.00% |

The cough drop is prepared by first mixing the hard candy previously cooked to between 260°-280° F. under a vacuum into a mechanical candy mixer and mixing the menthol-eucalyptus blend with the candy to form Part A. The hard candy outer shell is placed around a powder center-filling tube in a heated candy batch-former and filled with the powder blend in Part B and tabletted with conventional candy forming equipment.

When dissolved in the mouth, the exposure of the center-filling causes a rapid, perceptible vaporization of the active ingredient into the oral and nasal cavities.

What is claimed is:

1. A cough drop product having an outer hard candy base shell and a centerfill comprising a rapidly-dissolving powder and menthol-eucalyptus in powdered form.

2. The comestible of claim 1 wherein said rapidly-dissolving powder is selected from the group consisting of dextrose monohydrate, sorbitol, xylitol, sucrose and mixtures thereof.

3. The comestible of claim 1 wherein said rapidly-dissolving powder is dextrose monohydrate.

4. The comestible of claim 1 wherein said active ingredient is menthol-eucalyptus.

5. The comestible of claim 1 wherein said outer shell comprises a hard candy base of sucrose and corn syrup.

6. The comestible of claim 5 wherein said hard candy base outer shell further contains an active ingredient.

7. The comestible of claim 6 wherein said active ingredient is menthol-eucalyptus.

8. The comestible of claim 5 wherein said hard candy base further comprises an excipient selected from the group consisting of a food grade acid, flavorant, and a sweetener.

9. A cough drop comprising:
 (a) an outer shell comprised of a candy base and an active ingredient; and
 (b) a center having a powdered centerfill comprising a powder selected from the group consisting of dextrose monohydrate, sorbitol, xylitol, sucrose and mixtures thereof and menthol-eucalyptus in powdered form.

10. The cough drop of claim 9 wherein said powder comprises from 0.1% to 75% by weight of said powdered centerfill.

11. The cough drop of claim 9 wherein said active ingredient comprises from 0.002% to 2.000% by weight of said powdered centerfill.

12. The cough drop of claim 9 wherein said outer shell comprises from 55% to 99.9% by weight of the total weight of said cough drop.

13. The cough drop of claim 9 wherein said hard candy base further comprises an excipient selected from the group consisting of food grade acids, flavorants and sweeteners.

14. A cough drop comprising:
 (a) an outer shell comprised of a cooked mixture of sucrose and corn syrup and menthol and eucalyptus; and
 (b) a centerfill comprising dextrose monohydrate, a liquid blend of menthol and eucalyptus and a spray-dried powder of menthol and eucalyptus.

15. The cough drop of claim 14 wherein said dextrose monohydrate comprises from 5% to 35% by weight of said centerfill.

16. The cough drop of claim 14 wherein said liquid blend of menthol and eucalyptus comprises from 0.002% to 2.000% by weight of the centerfill.

17. The cough drop of claim 14 wherein said spray-dried powder of menthol and eucalyptus comprises from 0.1% to 35% by weight of said centerfill.

18. The cough drop of claim 14 wherein said sucrose and corn syrup comprises from 0.001% to 30% by weight of said total shell.

19. The cough drop of claim 14 wherein said menthol and eucalyptus comprises from 0.002% to 2% by weight of the total shell.

20. The cough drop of claim 14 which further comprises an excipient selected from the group consisting of a food grade acid, a flavorant and a sweetener.

* * * * *